United States Patent
Schlueter

(10) Patent No.: US 10,712,474 B2
(45) Date of Patent: Jul. 14, 2020

(54) HIGH REFRACTIVE INDEX, HIGH ABBE NUMBER INTRAOCULAR LENS MATERIALS

(71) Applicant: NOVARTIS AG, Basel (CH)

(72) Inventor: Douglas Schlueter, Azle, TX (US)

(73) Assignee: Alcon Inc., Fribourg (CH)

( * ) Notice: Subject to any disclaimer, the term of this patent is extended or adjusted under 35 U.S.C. 154(b) by 0 days.

(21) Appl. No.: 16/509,667

(22) Filed: Jul. 12, 2019

(65) Prior Publication Data

US 2019/0339419 A1 Nov. 7, 2019

Related U.S. Application Data

(62) Division of application No. 15/995,558, filed on Jun. 1, 2018, now Pat. No. 10,408,974.

(60) Provisional application No. 62/515,276, filed on Jun. 5, 2017.

(51) Int. Cl.
| | |
|---|---|
| *A61F 2/02* | (2006.01) |
| *B29D 11/00* | (2006.01) |
| *C08F 20/00* | (2006.01) |
| *G02B 1/04* | (2006.01) |
| *C08F 220/30* | (2006.01) |
| *A61L 27/16* | (2006.01) |
| *A61L 27/50* | (2006.01) |
| *G02C 7/10* | (2006.01) |
| *A61F 2/16* | (2006.01) |

(52) U.S. Cl.
CPC .............. *G02B 1/041* (2013.01); *A61L 27/16* (2013.01); *A61L 27/50* (2013.01); *C08F 220/30* (2013.01); *A61F 2002/16965* (2015.04); *A61L 2430/16* (2013.01); *G02C 7/108* (2013.01)

(58) Field of Classification Search
CPC ......... G02B 1/041; A61L 27/16; A61L 27/50; A61L 2430/16; C08F 220/30; G02C 7/108
See application file for complete search history.

(56) References Cited

U.S. PATENT DOCUMENTS

| | | | |
|---|---|---|---|
| 6,686,413 B2 | 2/2004 | Nakamura et al. | |
| 2006/0286147 A1* | 12/2006 | Salamone | A61L 27/18 424/427 |
| 2010/0314591 A1* | 12/2010 | Roitman | C08F 220/18 252/589 |

FOREIGN PATENT DOCUMENTS

WO 2010/144763 A2 12/2010

* cited by examiner

*Primary Examiner* — Bijan Ahvazi
(74) *Attorney, Agent, or Firm* — Patrick M. Ryan

(57) ABSTRACT

Disclosed are high refractive index, hydrophobic, acrylic materials. These materials have both high refractive index and a high Abbe number. This combination means the materials have a low refractive index dispersion and thus are especially suitable for use as intraocular lens materials. The materials are also suitable for use in other implantable ophthalmic devices, such as keratoprostheses, corneal rings, corneal implants, and corneal inlays.

17 Claims, No Drawings

HIGH REFRACTIVE INDEX, HIGH ABBE NUMBER INTRAOCULAR LENS MATERIALS

This application is a divisional application of U.S. Ser. No. 15/995,558, filed Jun. 1, 2018, which claims priority from provisional application Ser. No. 62/515,276, filed Jun. 5, 2017.

FIELD OF THE INVENTION

This invention is directed to acrylic device materials. In particular, this invention relates to high refractive index acrylic device materials particularly suited for use as intraocular lens ("IOL") materials, which can be injected through small incisions of less than 2.5 mm.

BACKGROUND OF THE INVENTION

With the recent advances in small-incision cataract surgery, increased emphasis has been placed on developing soft, foldable materials suitable for use in artificial lenses. In general, these materials fall into one of three categories: hydrogels, silicones, and acrylics.

In general, hydrogel materials have a relatively low refractive index, making them less desirable than other materials because of the thicker lens optic necessary to achieve a given refractive power. Silicone materials generally have a higher refractive index than hydrogels, but tend to unfold explosively after being placed in the eye in a folded position. Explosive unfolding can potentially damage the corneal endothelium and/or rupture the natural lens capsule. Acrylic materials are desirable because they typically have a higher refractive index than silicone materials and unfold more slowly or controllably than silicone materials.

U.S. Pat. No. 5,290,892 discloses high refractive index, acrylic materials suitable for use as an IOL material. These acrylic materials contain, as principal components, two aryl acrylic monomers. They also contain a cross-linking component. The IOLs made of these acrylic materials can be rolled or folded for insertion through small incisions.

U.S. Pat. No. 5,331,073 also discloses soft acrylic IOL materials. These materials contain as principal components, two acrylic monomers which are defined by the properties of their respective homopolymers. The first monomer is defined as one in which its homopolymer has a refractive index of at least about 1.50. The second monomer is defined as one in which its homopolymer has a glass transition temperature less than about 22° C. These IOL materials also contain a cross-linking component. Additionally, these materials may optionally contain a fourth constituent, different from the first three constituents, which is derived from a hydrophilic monomer. These materials preferably have a total of less than about 15% by weight of a hydrophilic component.

U.S. Pat. No. 5,693,095 discloses foldable ophthalmic lens materials comprising a total of at least 90% by weight of only two principal lens-forming monomers. One lens-forming monomer is an aryl acrylic hydrophobic monomer. The other lens-forming monomer is a hydrophilic monomer. The lens materials also comprise a cross-linking monomer and optionally comprise a UV absorber, polymerization initiators, reactive UV absorbers and reactive blue-light absorbers.

U.S. Pat. No. 6,653,422 discloses foldable ophthalmic lens materials consisting essentially of a single device-forming monomer and at least one cross-linking monomer. The materials optionally contain a reactive UV absorber and optionally contain a reactive blue-light absorber. The single device-forming monomer is present in an amount of at least about 80% by weight. The device-forming monomer is an aryl acrylic hydrophobic monomer.

Acrylic materials with a higher refractive index have historically been preferred as IOL materials because less material is required to make a lens of a given dioptric power. Thus a lens made from a higher refractive index material may be implanted through a smaller incision than a similar power lens made from a lower refractive index material. Use of a smaller incision in turn results in fewer traumas and reduces the likelihood of surgically induced astigmatism. However, polymer materials with high refractive index also generally exhibit refractive index dispersion. This can result in chromatic aberrations that may impact visual performance when viewing light of differing wavelengths.

In general, the presence of aromatic groups leads to materials with higher refractive index dispersion. Hydrophobic acrylic materials without aromatic groups will have reduced refractive index dispersion but will also have lower refractive index, thus will require a larger incision size than a comparable lens made from a high refractive index polymer.

SUMMARY OF THE INVENTION

Improved soft, foldable acrylic materials which are particularly suited for use as IOLs, but which are also useful as other implantable ophthalmic devices, such as keratoprostheses, corneal rings, corneal implants, and corneal inlays have now been discovered. These materials have both high refractive index and low refractive index dispersion. This is accomplished using monomers containing cycloaliphatic functional groups in a hydrophobic acrylic polymer. The materials of the present invention are copolymers formed by polymerizing a mixture comprising a major amount of a cycloaliphatic hydrophobic acrylic monomer, a hydrophilic monomer, and a cross-linking agent.

The implantable ophthalmic device materials of the present invention are optically clear such that they are suitable for use as IOLs and they have low tack, low surface scatter, good stability profile, and good delivery properties. Among other factors, the present invention is based on the finding that a multi-component, copolymeric, high refractive index device material obtained by copolymerizing the ingredients mentioned above is soft, glistening-free, has low tack and low haze, has low surface light scatter, and is capable of going through small (2.5 mm or less) incisions with good unfolding properties.

DETAILED DESCRIPTION OF THE INVENTION

Unless indicated otherwise, all component amounts are presented on a % (w/w) basis ("wt. %").

The ophthalmic device materials of the present invention comprise a major amount of a cycloaliphatic acrylic monomer having the formula:

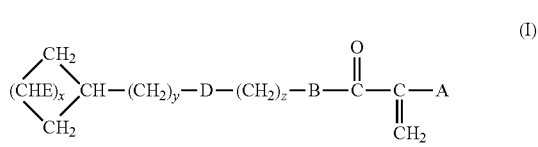

wherein: A is H or $CH_3$;
B is O, NR, or S;
D is O, S, or nothing (i.e., a single bond);
E is $CH_3$, $CH_2CH_3$, $CH(CH_3)_2$, $C(CH_3)_3$, $CH_2OH$ or H;
R is H, $CH_3$, $CH_2CH_3$, or $CH(CH_3)_2$;
x is 1-4, provided that if x is >1, then not more than one CHE group has E≠H;
y is 0-2; and
z is 0-4, provided that if D=nothing, then z≠0.

Preferred acrylic hydrophobic monomers for use in the materials of the present invention are those wherein B is O, z is 0-2, D is O or nothing, y is 0, x is 2 or 3, and E is independently H, $CH_2OH$ or $CH_3$, provided if z=0 or 1, then D is nothing. Most preferred is B is O, z is 2, D is nothing, y is 0, x is 3, and E is H. For example, preferred monomers include 2-cyclohexylethyl acrylate, 2-cyclopentylethyl acrylate, 3-cyclohexylpropyl acrylate, 3-cyclopentylpropyl acrylate and 2-(cyclohexyloxy)ethyl acrylate. Most preferred is 2-cyclohexylethyl acrylate.

Monomers of formula I can be made by known methods. For example, the conjugate alcohol of the desired monomer can be combined in a reaction vessel with methyl acrylate, tetrabutyl titanate (catalyst), and a polymerization inhibitor such as 4-benzyloxy phenol. The vessel can then be heated to facilitate the reaction and distill off the reaction by-products to drive the reaction to completion. Alternative synthesis schemes involve adding acrylic acid to the conjugate alcohol and catalyzing with a carbodiimide or mixing the conjugate alcohol with acryloyl chloride and a HCl acceptor such as pyridine or triethylamine.

The monomeric mixture polymerized to obtain the materials of the present invention comprises a total of 70-90%, preferably 75-85%, and more preferably 77-82% one or more monomers of formula (I).

is In addition to the monomer of formula (I), the mixture polymerized to form the materials of the present invention also contains a hydrophilic monomer selected from the group consisting of: hydroxy($C_2$-$C_4$ alkyl)methacrylates, glycerol methacrylate, and N-vinyl pyrrolidone. Hydroxy ($C_2$-$C_4$ alkyl)methacrylates are preferred. The most preferred hydrophilic monomer is 2-hydroxyethyl methacrylate. The mixture or solution to be polymerized will contain a total amount of hydrophilic monomer of 5-25%, preferably 12-22%, and more preferably 16-19%. The total amount of hydrophilic monomers contained in the materials of the present invention should be limited such that the equilibrium water content (at 35° C.) of the polymerized device material of the present invention is less than 4%, and preferably less than 2%.

The copolymer materials of the present invention are cross-linked. The copolymerizable cross-linking agent used in the copolymers of this invention may be any terminally ethylenically unsaturated compound having more than one unsaturated group. Suitable cross-linking agents include, for example low molecular weight cross-linking agents having a molecular weight from 100-500 Daltons and high molecular weight cross-linking agents having a molecular weight from 501-6,000 Daltons. Low molecular cross-linking agents will typically be present in a total amount from 0.5-3%, whereas high molecular weight cross-linking agents will typically be present in a total amount from 2-15%. In general, the total amount of cross-linking agent in the materials of the present invention will range from 0.5-10%, and will preferably range from 1-3% of low molecular weight cross-linker or 3-10% of a high molecular weight cross-linker.

Suitable low molecular weight cross-linking agents include: ethylene glycol diacrylate; diethylene glycol diacrylate; allyl acrylate; 1,3-propanediol diacrylate; 2,3-propanediol diacrylate; 1,6-hexanediol diacrylate; 1,4-butanediol diacrylate; triethylene glycol diacrylate; cyclohexane-1,1-diyldimethanol diacrylate, 1,4-cyclohexanediol diacrylate, 1,3-adamantanediol diacrylate, 1,3-adamantanedimethyl diacrylate, 2,2-diethyl-1,3-propanediol diacrylate, 2,2-diisobutyl-1,3-propanediol diacrylate, 1,3-cyclohexanedimethyl diacrylate, 1,4-cyclohexanedimethyl diacrylate; neopentyl glycol diacrylate; and their corresponding methacrylates. Preferred low molecular cross-linking monomers include 1,4-butanediol diacrylate; 1,4-cyclohexanedimethyl diacrylate; and neopentyl glycol diacrylate. Most preferred is neopentyl glycol diacrylate. Suitable high molecular weight cross-linking agents include poly(ethylene glycol) dimethacrylate ($M_n$=700 Daltons) and poly(ethylene glycol) dimethacrylate ($M_n$=2000 Daltons).

In a preferred embodiment, the mixture used to form the materials of the present invention contains 0.5-2%, preferably 1.4-1.8%, neopentyl glycol diacrylate.

In addition to the monomer of formula (I), the hydrophilic monomer, and the cross-linking agent, the mixture used to form the materials of the present invention preferably also contains a reactive (polymerizable) UV absorber and optionally contains a reactive blue-light absorber.

Many reactive UV absorbers are known. Preferred reactive UV absorbers are 2-(2'-hydroxy-3'-methallyl-5'-methylphenyl)benzotriazole, commercially available as o-Methallyl Tinuvin P ("oMTP") from Polysciences, Inc., Warrington, Pa., 3-(2H-benzo[d][1,2,3]triazol-2-yl)-4-hydroxyphenylethyl methacrylate, and 2-(3-(tert-butyl)-4-hydroxy-5-(5-methoxy-2H-benzo[d][1,2,3]triazol-2-yl)pheno) ethyl methacrylate. UV absorbers are typically present in an amount from 0.1-5 wt. %. In one embodiment, the materials of the present invention contain 1.5-2.5 wt. %, preferably 1.5-2 wt. %, of a reactive UV absorber.

Many reactive blue-light absorbing compounds are known. Preferred reactive blue-light absorbing compounds are those described in U.S. Pat. Nos. 5,470,932; 8,207,244; and 8,329,775, the entire contents of which are hereby incorporated by reference. A preferred blue-light absorbing dye is N-2-[3-(2'-methylphenylazo)-4-hydroxyphenyl]ethyl methacrylamide. When present, blue-light absorbers are typically present in an amount from 0.005-1 wt. %, preferably 0.01-0.1 wt. %.

Although the monomer mixture that is polymerized to form the ophthalmic device materials of the present invention contains a monomer of formula (I), a hydrophilic monomer, a cross-linking agent, preferably contains a UV absorber, and optionally contains a blue-light absorber, it preferably does not contain any aromatic monomer.

The implantable ophthalmic device materials of the present invention are prepared by combining the ingredients described above and polymerizing the resulting mixture. Suitable polymerization initiators include thermal initiators and photoinitiators. Preferred thermal initiators include peroxy free-radical initiators, such as t-butyl (peroxy-2-ethyl) hexanoate; and di-(tert-butylcyclohexyl) peroxydicarbonate (commercially available as Perkadox® 16 from Akzo Chemicals Inc., Chicago, Ill.), or azo initiators, such as 2,2'-(diazene-1,2-diyl)bis(2,4-dimethylpentanenitrile. A preferred photoinitiator is phenylphosphorylbis(mesitylmethanone), which is commercially available as Irgacure® 819. Initiators are typically present in an amount of 3 wt. % or less, and preferably 1.5 wt. % or less. Customarily, the total amount of initiator is not included when determining the amounts of other ingredients in copolymeric compositions.

The identity and amount of the principal monomer component (the monomer of formula (I)) described above and the identity and amount of any additional components are determined by the desired properties of the finished ophthalmic lens material. Preferably, the ingredients and their proportion are selected so that the acrylic device materials of the present invention possess the following properties, which make the materials of the present invention particularly suitable for use in IOLs which are to be inserted through incisions of 2.5 mm or less, and preferably 2.0 mm or less.

The lens material preferably has a refractive index of 1.46-1.50, preferably 1.48-1.50, and most preferably 1.49-1.50. Despite having a relatively high refractive index, the materials of the present invention have an Abbe No. greater than 47, preferably greater than 50, and most preferably, greater than 52. Refractive index and Abbe No. are both measured using an Abbe refractometer and a material sample that has been equilibrated in balanced salt solution at 35° C. prior to measurement. Refractive index measurements are taken at 589 nm (Na light source). The Abbe number ($v_D$) is calculated using the following formula:

$$v_D = (n_D-1)/(n_F-n_C)$$

where $n_D$, $n_F$, and $n_C$ are the refractive indices of the material at 589 nm (sodium D), 486 nm (hydrogen F), and 656 nm (hydrogen C), respectively The glass-transition temperature ("Tg") of the lens material, which affects the material's folding and unfolding characteristics, is preferably below about 15° C., and more preferably below about 10° C. Tg is measured by differential scanning calorimetry at 10° C./min., and is determined as the half-height of the heat capacity increase.

The lens material will have an elongation (strain at break) of at least 110%, preferably at least 120%, and most preferably at least 130%. This property indicates that the lens generally will not crack, tear or split when folded. Elongation of polymer samples is determined on dumbbell shaped tension test specimens with a 20 mm total length, length in the grip area of 11 mm, overall width of 2.49 mm, 0.833 mm width of the narrow section, a fillet radius of 8.83 mm, and a thickness of 0.9 mm. Testing is performed on samples at either 18±2° C. or 23±2° C. and 50±10% relative humidity using a tensile tester. The grip distance is set at 11 mm and a crosshead speed is set at 50-mm/minute and the sample is pulled to failure. The strain at break is reported as a fraction of the displacement at failure to the original grip distance. Stress at break is calculated at the maximum load for the sample, typically the load when the sample breaks, assuming that the initial area remains constant. The Young's modulus is calculated from the instantaneous slope of the stress-strain curve in the linear elastic region. The 25% secant modulus is calculated as the slope of a straight line drawn on the stress-strain curve between 0% strain and 25% strain. The 100% secant modulus is calculated as the slope of a straight line drawn on the stress-strain curve between 0% strain and 100% strain.

The lens material will have an equilibrium water content (EWC) of less than <4%. EWC is gravimetrically determined using an analytical balance. First, the dry sample weight is obtained, then the sample is equilibrated in balanced salt solution (BSS) at ambient temperature for at least 24 h. The sample is then removed from the BSS, excess surface liquid is removed and the sample is weighed. % EWC is determined by the following formula:

$$\% \ EWC = \frac{(wt_{hydrated} - wt_{dry})}{wt_{hydrated}} \times 100$$

Glistening evaluation was carried out by placing samples in deionized water at 45° C. for 20 hours. The samples are then transferred to a 37° C. bath Samples were inspected for glistenings after 2 hours of cooling to 37° C. using an optical microscope under dark field conditions with a magnification of at least 100×. The average number of glistenings per $mm^2$ in the sample is determined. Preferably, the materials of the present invention have less than 10 glistenings/$mm^2$, and more preferably less than 1 glistening/$mm^2$.

IOLs constructed of the materials of the present invention can be of any design capable of being rolled or folded into a small cross section that can fit through a relatively smaller incision. For example, the IOLs can be of what is known as a one piece or multipiece design, and comprise optic and haptic components. The optic is that portion which serves as the lens. The haptics are attached to the optic and hold the optic in its proper place in the eye. The optic and haptic(s) can be of the same or different material. A multipiece lens is so called because the optic and the haptic(s) are made separately and then the haptics are attached to the optic. In a single piece lens, the optic and the haptics are formed out of one piece of material. Depending on the material, the haptics are then cut, or lathed, out of the material to produce the IOL.

The invention will be further illustrated by the following examples, which are intended to be illustrative, but not limiting.

EXAMPLES

Monomer solutions were prepared by combining ingredients in proportions as listed in Tables 1-4 below. Each solution was thoroughly mixed and bubbled with $N_2$. The monomer solution was filtered through a 0.2 micron PTFE membrane directly into polypropylene lens molds or rectangular flat molds. For Examples 1-5, the filled molds were placed in an oven and heated to 70° C. for 1 hr, followed by a 2 hr post cure at 100° C. Once cooled, the product was removed from the molds, extracted in acetone at ambient temperature, rinsed with fresh acetone and allowed to air dry. The product was then placed under vacuum at 70° C. for at least 16h. For Examples 6-22, the filled molds were placed in a preheated 105° C. oven for 20 min, followed by a 2 hr 40 min post cure at 100° C. Once cooled, the product was removed from the molds, extracted in ethanol at ambient temperature, rinsed with fresh ethanol and allowed to air dry. The product was then placed under vacuum at 80° C. for at least 16h. Prior to delivery testing the IOL samples were Argon plasma treated for 1 min (400 W, 160 mTorr) to reduce tackiness (see, e.g., U.S. Pat. No. 5,603,774). Tensile properties, refractive index, Abbe no., glistenings, and EWC were determined as described above. Tensile properties were measured using an Instron Material Tester Model No. 4442 with a 50 N load cell using a crosshead speed of 50 mm/min. Refractive index and Abbe number were measured using an ATAGO DR-M2 multi-wavelength Abbe refractometer.

TABLE 1

Examples 1-5

|  | EX 1 | EX 2 | EX 3 | EX 4 | EX 5 |
| --- | --- | --- | --- | --- | --- |
| CHEA (wt. %) | 81.62 | 76.57 | 78.54 | 78.23 | 78.40 |
| HEMA (wt. %) | 15.03 | 20.07 | 18.07 | 18.03 | 18.09 |
| BDDA (wt. %) | 1.55 | 1.56 | 1.63 | — | — |
| CHDA (wt. %) | — | — | — | 1.92 | — |
| NPGDA (wt. %) | — | — | — | — | 1.69 |
| oMTP (wt. %) | 1.80 | 1.80 | 1.75 | 1.81 | 1.82 |
| Perkdox16 (wt. % of total formulation) | 1.00 | 0.99 | 0.99 | 0.99 | 1.01 |
| RI (BSS, 35° C.) | 1.497 | 1.496 | — | 1.497 | 1.497 |
| Abbe No (BSS, 35° C.) | 55.2 ± 0.0 | 57.9 ± 4.7 | — | 55.4 ± 1.0 | 54.7 ± 2.1 |
| EWC (BSS, 23° C.) | 0.72 ± 0.10 | 1.63 ± 0.05 | 0.84 | 1.14 ± 0.16 | 0.88 ± 0.08 |
| Glistenings (MV/mm$^2$) | <5 | <1 | <1 | <10 | <1 |
| $T_{g, start}$ (° C.) | −12.5 | −8.4 | −7.4 | −7.1 | −6.2 |
| $T_{g, mid}$ (° C.) | −7.0 | −3.9 | −2.9 | −2.1 | −1.5 |
| $T_{g, end}$ (° C.) | −1.6 | 0.7 | 1.6 | 2.8 | 3.1 |
| Stress at Break (MPa) | 1.64 ± 0.21 | 4.88 ± 0.40 | 3.22 ± 0.33 | 3.28 ± 0.28 | 3.81 ± 0.29 |
| Strain at Break (%) | 137.2 ± 7.7 | 140.1 ± 4.2 | 141.4 ± 5.8 | 132.1 ± 6.9 | 161.3 ± 6.7 |
| Young's Modulus (MPa) | 11.55 ± 2.33 | 34.14 ± 4.29 | 19.10 ± 1.57 | 22.35 ± 2.58 | 21.02 ± 2.69 |
| 25% Secant Modulus | 1.37 ± 0.05 | 4.76 ± 0.59 | 2.59 ± 0.05 | 2.83 ± 0.13 | 2.69 ± 0.10 |
| 100% Secant Modulus | 1.01 ± 0.03 | 3.36 ± 0.40 | 1.90 ± 0.04 | 2.16 ± 0.07 | 1.89 ± 0.02 |
| Instron test temp (° C.) | 24.5 | 24.3 | 24.4 | 24.6 | 24.6 |

CHEA = 2-cyclohexylethyl acrylate
HEMA = 2-hydroxyethyl methacrylate
BDDA = 1,4-butanediol diacrylate
CHDA = 1,4-cyclohexanediemthyl diacrylate
NPGDA = neopentyl glycol diacrylate
oMTP = 2-(2'-hydroxy-3'-methallyl-5'-methylphenyl)benzotriazole
Perkadox16 = Di(4-tert-butylcyclohexyl) peroxydicarbonate

TABLE 2

Examples 6-10

|  | EX 6 | EX 7 | EX 8 | EX 9 | EX 10 |
| --- | --- | --- | --- | --- | --- |
| CHEA (wt. %) | 78.78 | 78.38 | 78.58 | 78.58 | 78.58 |
| HEMA (wt. %) | 18.00 | 18.00 | 18.00 | 18.00 | 18.00 |
| NPGDA (wt. %) | 1.62 | 1.62 | 1.62 | 1.62 | 1.62 |
| oMTP (wt. %) | 1.60 | 2.00 | 1.80 | 1.80 | 1.80 |
| Perkdox16 (wt % of total formulation) | 1.50 | 1.50 | 1.75 | 1.25 | 1.50 |
| Young's modulus (MPa) | 89.79 ± 5.10 | 105.38 ± 9.83 | 103.44 ± 8.24 | 96.91 ± 4.79 | 103.7 ± 8.36 |
| Secant modulus, 25% (MPa) | 10.28 ± 0.36 | 11.34 ± 0.26 | 11.35 ± 0.24 | 11.05 ± 0.15 | 10.93 ± 0.35 |
| Secant modulus, 100% (MPa) | 5.02 ± 0.16 | 5.32 ± 0.10 | 5.39 ± 0.12 | 5.16 ± 0.06 | 5.15 ± 0.18 |
| Tensile strength (MPa) | 9.89 ± 0.89 | 9.90 ± 1.34 | 9.61 ± 0.91 | 9.40 ± 0.96 | 9.88 ± 0.79 |
| Strain at break (%) | 184.7 ± 11.5 | 179.4 ± 17.0 | 177.0 ± 10.7 | 180.4 ± 12.3 | 189.7 ± 12.9 |

TABLE 3

Examples 11-16

|  | EX 11 | EX 12 | EX 13 | EX 14 | EX 15 | EX 16 |
| --- | --- | --- | --- | --- | --- | --- |
| CHEA | 80.80 | 80.58 | 80.40 | 79.80 | 79.58 | 79.40 |
| HEMA | 16.00 | 16.00 | 16.00 | 17.00 | 17.00 | 17.00 |
| NPGDA | 1.40 | 1.62 | 1.80 | 1.40 | 1.62 | 1.80 |
| oMTP | 1.80 | 1.80 | 1.80 | 1.80 | 1.80 | 1.80 |
| Secant modulus (25%) | 6.28 ± 0.15 | 7.04 ± 0.28 | 7.32 ± 0.26 | 7.58 ± 0.11 | 8.28 ± 0.32 | 8.71 ± 0.26 |
| Secant modulus (100%) | 3.28 ± 0.06 | 3.62 ± 0.14 | 3.90 ± 0.15 | 3.81 ± 0.05 | 4.20 ± 0.14 | 4.48 ± 0.14 |
| Tensile strength | 7.23 ± 0.41 | 6.42 ± 0.98 | 7.81 ± 1.13 | 8.58 ± 0.49 | 7.87 ± 0.63 | 7.96 ± 1.01 |
| % Strain at break | 184 ± 6 | 168 ± 20 | 172 ± 12 | 189 ± 5 | 170 ± 7 | 166 ± 13 |
| SSNG (PBS, n = 5) | 17.2 ± 3.2 | 17.1 ± 6.2 | 10.1 ± 2.1 | 14.4 ± 2.9 | 20.4 ± 5.6 | 8.9 ± 2.0 |
| Glistening density (vac/mm$^2$) | 0.1 ± 0.3 | 0.1 ± 0.4 | 0.1 ± 0.4 | 0.1 ± 0.3 | 0 | 0 |

TABLE 4

Examples 17-22

|  | EX 17 | EX 18 | EX 19 | EX 20 | EX 21 | EX 22 |
|---|---|---|---|---|---|---|
| CHEA | 78.80 | 78.58 | 78.40 | 77.80 | 77.58 | 77.40 |
| HEMA | 18.00 | 18.00 | 18.00 | 19.00 | 19.00 | 19.00 |
| NPGDA | 1.40 | 1.62 | 1.80 | 1.40 | 1.62 | 1.80 |
| oMTP | 1.80 | 1.80 | 1.80 | 1.80 | 1.80 | 1.80 |
| Secant modulus (25%) | 9.50 ± 0.50 | 10.07 ± 0.38 | 11.13 ± 0.29 | 11.94 ± 0.30 | 12.54 ± 0.31 | 11.62 ± 0.59 |
| Secant modulus (100%) | 4.61 ± 0.19 | 4.97 ± 0.20 | 5.50 ± 0.12 | 5.54 ± 0.15 | 5.92 ± 0.09 | 5.67 ± 0.22 |
| Tensile strength | 8.88 ± 0.86 | 8.44 ± 0.66 | 9.02 ± 0.52 | 8.91 ± 1.12 | 9.28 ± 0.73 | 9.16 ± 0.56 |
| % Strain at break | 184 ± 15 | 166 ± 5 | 161 ± 9 | 166 ± 7 | 157 ± 8 | 158 ± 6 |
| SSNG (PBS, n = 5) | 21.7 ± 1.6 | 16.6 ± 9.1 | 9.7 ± 5.7 | 15.2 ± 1.2 | 12.9 ± 3.1 | 12.8 ± 5.4 |
| Glistening density (vac/mm$^2$) | ND | 0.1 ± 0.3 | ND | ND | ND | ND |

Example 23

Delivery Evaluation of Lenses

Lenses cast in 40 Diopter molds from select formulations were delivered through Monarch III D cartridges using H4 handpieces (with and without soft tip) and Viscoat viscoelastic. Lens delivery was carried out at 18° C. and 23° C. with no dwell time. Post-delivery evaluations included optic and haptic damage as well as delivery cartridge damage. In general, all the lens optics unfolded quickly and haptics did not stick to the optic region upon delivery. In addition, optics, haptics, and delivery cartridges passed post-delivery cosmetic inspection.

The invention having now been fully described, it should be understood that it may be embodied in other specific forms or variations without departing from its spirit or essential characteristics. Accordingly, the embodiments described above are to be considered in all respects as illustrative and not restrictive, the scope of the invention being indicated by the appended claims rather than by the foregoing description, and all changes which come within the meaning and range of equivalency of the claims are intended to be embraced therein.

I claim:

1. A polymeric ophthalmic device material made by polymerizing a mixture of monomers wherein the mixture comprises:
   a) a total of 70-90 wt. % of one or more cycloaliphatic acrylic monomers of formula (I)

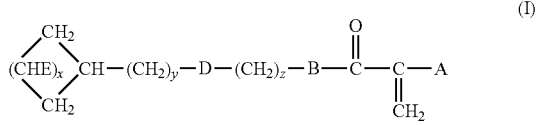

(I)

wherein: A is H or $CH_3$;
B is O, NR, or S;
D is O, S, or nothing;
E is $CH_3$, $CH_2CH_3$, $CH(CH_3)_2$, $C(CH_3)_3$, $CH_2OH$ or H;
R is H, $CH_3$, $CH_2CH_3$, or $CH(CH_3)_2$;
x is 1-4, provided that if x is >1, then not more than one CHE group has E≠H;
y is 0-2; and
z is 0-4, provided that if D=nothing, then z≠0.

b) a total of 5-25 wt. % of one or more hydrophilic monomers selected from the group consisting of: hydroxy($C_2$-$C_4$ alkyl)methacrylates, glycerol methacrylate, and N-vinyl pyrrolidone; and
   c) a copolymerizable cross-linking agent;
   wherein the ophthalmic device material has a refractive index of 1.46-1.50 and an Abbe number greater than 47, a Tg<15° C., and an equilibrium water content of the polymerized ophthalmic device material is less than 4%.

2. The ophthalmic device material of claim 1, wherein for the cycloaliphatic acrylic monomer of formula (I):
   A is H or $CH_3$;
   B is O;
   D is O or nothing;
   E is $CH_3$ or H;
   x is 2-2, provided that not more than one CHE group has E=$CH_3$;
   y is 0; and
   z is 0-2, provided that if D=nothing, then z≠0.

3. The ophthalmic device material of claim 2, wherein for the cycloaliphatic acrylic monomer of formula (I):
   A is H or $CH_3$;
   B is O;
   D is nothing;
   E is H;
   x is 3;
   y is 0; and
   z is 2.

4. The ophthalmic device material of claim 1, wherein the cycloaliphatic acrylic monomer of formula (I) is selected from the group consisting of: 2-cyclohexylethyl acrylate; 2-cyclopentylethyl acrylate; 3-cyclohexylpropyl acrylate; 3-cyclopentylpropyl acrylate; and 2-(cyclohexyloxy)ethyl acrylate.

5. The ophthalmic device material of claim 1, wherein the mixture comprises a total of 75-85 wt. % of cycloaliphatic acrylic monomer of formula (I).

6. The ophthalmic device material of claim 5, wherein the mixture comprises a total of 77-82 wt. % of cycloaliphatic acrylic monomer of formula (I).

7. The ophthalmic device material of claim 1, wherein the hydrophilic monomer is a hydroxy($C_2$-$C_4$ alkyl)methacrylate and the mixture comprises a total of 12-22 wt. % of hydrophilic monomer.

8. The ophthalmic device material of claim 7, wherein the hydrophilic monomer is 2-hydroxethyl methacrylate.

9. The ophthalmic device material of claim 8, wherein the mixture comprises a total of 16-19 wt. % of 2-hydroxethyl methacrylate.

10. The ophthalmic device material of claim 1, wherein the equilibrium water content of the polymerized ophthalmic device material is less than 2%.

11. The ophthalmic device material of claim 1, wherein the copolymerizable cross-linking agent is a terminally ethylenically unsaturated compound having more than one unsaturated group.

12. The ophthalmic device material of claim 11, wherein the copolymerizable cross-linking agent is selected from the group consisting of: ethylene glycol diacrylate; diethylene glycol diacrylate; allyl acrylate; 1,3-propanediol diacrylate; 2,3-propanediol diacrylate; 1,6-hexanediol diacrylate; 1,4-butanediol diacrylate; triethylene glycol diacrylate; cyclohexane-1,1-diyldimethanol diacrylate, 1,4-cyclohexanediol diacrylate, 1,3-adamantanediol diacrylate, 1,3-adamantanedimethyl diacrylate, 2,2-diethyl-1,3-propanediol diacrylate, 2,2-diisobutyl-1,3-propanediol diacrylate, 1,3-cyclohexanedimethyl diacrylate, 1,4-cyclohexanedimethyl diacrylate; neopentyl glycol diacrylate; ethylene glycol dimethacrylate; diethylene glycol dimethacrylate; allyl methacrylate; 1,3-propanediol dimethacrylate; 2,3-propanediol dimethacrylate; 1,6-hexanediol dimethacrylate; 1,4-butanediol dimethacrylate; triethylene glycol dimethacrylate; cyclohexane-1,1-diyldimethanol dimethacrylate, 1,4-cyclohexanediol dimethacrylate, 1,3-adamantanediol dimethacrylate, 1,3-adamantanedimethyl dimethacrylate, 2,2-diethyl-1,3-propanediol dimethacrylate, 2,2-diisobutyl-1,3-propanediol dimethacrylate, 1,3-cyclohexanedimethyl dimethacrylate, 1,4-cyclohexanedimethyl dimethacrylate; neopentyl glycol dimethacrylate; poly(ethylene glycol) dimethacrylate ($M_n$=700 Daltons) and poly(ethylene glycol) dimethacrylate ($M_n$=2000 Daltons).

13. The ophthalmic device material of claim 12, wherein the mixture comprises 0.5-2 wt. % neopentyl glycol diacrylate.

14. The ophthalmic device material of claim 1, wherein the mixture comprises a total of 0.5-10 wt. % of cross-linking agent.

15. The ophthalmic device material of claim 1, wherein the mixture comprises 0.1-5 wt. % of a reactive UV absorber.

16. The ophthalmic device material of claim 1, wherein the ophthalmic device material has an Abbe number greater than 50.

17. An ophthalmic device material made by polymerizing a mixture of monomers wherein the mixture comprises:
 a) 75-85 wt. % 2-cyclohexylethyl acrylate;
 b) 12-22 wt. % 2-hydroxethyl methacrylate; and
 c) 1-3 wt. % of a cross-linking agent having a molecular weight of 100-500 Daltons;
 wherein the ophthalmic device material has a refractive index of 1.48-1.50, an Abbe number greater than 52, a Tg<15° C., and an equilibrium water content less than 2%.

* * * * *